United States Patent [19]
Luedtke, Jr.

[11] Patent Number: 5,574,208
[45] Date of Patent: *Nov. 12, 1996

[54] HYBRID CORN PLANT (3893)

[75] Inventor: Roy Luedtke, Jr., Grand Forks County, N. Dak.

[73] Assignee: Pioneer Hi-Bred International, Inc., Des Moines, Iowa

[*] Notice: The portion of the term of this patent subsequent to Jan. 24, 2014, has been disclaimed.

[21] Appl. No.: 361,895

[22] Filed: Dec. 22, 1994

Related U.S. Application Data

[63] Continuation of Ser. No. 187,966, Jan. 28, 1994, abandoned.

[51] Int. Cl.$^6$ .............................. A01H 1/02; A01H 4/00; A01H 5/00; A01H 5/04
[52] U.S. Cl. ................. 800/200; 800/250; 800/DIG. 56; 435/240.4; 435/240.49; 435/240.47; 435/240.5; 47/58; 47/DIG. 1
[58] Field of Search .................................... 800/200, 205, 800/235, 250, DIG. 56; 435/240.1, 240.4, 240.47, 240.49, 240.5; 47/58.01, 58.03, 58, DIG. 1

[56] References Cited

U.S. PATENT DOCUMENTS 4,812,599  3/1989  Segebart .................................. 800/200

FOREIGN PATENT DOCUMENTS 160390  11/1985  European Pat. Off. .

OTHER PUBLICATIONS

Conger, B. V., et al. (1987) "Somatic Embryogenesis From Cultured Leaf Segments of *Zea Mays*", *Plant Cell Reports*, 6:345–347.
Duncan, D. R., et al. (1985) "The Production of Callus Capable of Plant Regeneration From Immature Embryos of Numerous *Zea Mays* Genotypes", *Planta*, 165:322–332.
Edallo, et al. (1981) "Chromosomal Variation and Frequency of Spontaneous Mutation Associated with in Vitro Culture and Plant Regeneration in Maize", *Maydica*, XXVI: 39–56.
Green, et al., "Plant Regeneration From Tissue Cultures of Maize", *Crop Science*, vol. 15, pp. 417–421.
Green, C. E., et al. (1982) "Plant Regeneration in Tissue Cultures of Maize" *Maize for Biological Research*, pp. 367–372.
Hallauer, A. R. et al. (1988) "Corn Breeding" *Corn and Corn Improvement*, No. 18, pp. 463–481.
Meghji, M. R., et al. (1984). "Inbreeding Depression, Inbred & Hybrid Grain Yields, and Other Traits of Maize Genotypes Representing Three Eras", *Crop Science*, vol. 24, pp. 545–549.
Phillips, et al. (1988) "Cell/Tissue Culture and In Vitro Manipulation", *Corn & Corn Improvement*, 3rd Ed., ASA Publication, No. 18, pp. 345–349 & 356–357.
Poehlman (1987) *Breeding Field Crop*, AVI Publication Co., Westport, Ct., pp. 237–246.
Rao, K. V., et al., "Somatic Embryogenesis in Glume Callus Cultures", Osmania University, Hyberabad, India.
Sass, John F. (1977) "Morphology", *Corn & Corn Improvement*, ASA Publication. Madison, Wisconsin, pp. 89–109.
Songstad, D. D. et al. (1988) "Effect of ACC (1–aminocyclopropane–1–carboxylic acid), Silver Nitrate & Norbornadiene on Plant Regeneration From Maize Callus Cultures", *Plant Cell Reports*, 7:262–265.
Tomes, et al. 1985. "The Effect of Parental Genotype on Initiation of Embryogenic Callus From Elite Maize (*Zea Mays* L.) Germplasm", *Theor. Appl. Genet.*, vol. 70, pp. 505–509.
Troyer, et al. (1985) "Selection for Early Flowering in Corn: 10 Late Synthetics", *Crop Science*, vol. 25, pp. 695–697.
Umbeck, et al. 1983. "Reversion of Male–Sterile T–Cytoplasm Maize to Male Fertility in Tissue Culture", *Crop Science*, vol. 23, pp. 584–588.
Wright, Harold (1980) "Commercial Hybrid Seed Production", *Hybridizaton of Crop Plants*, Ch. 8: 161–176.
Wych, Robert D. (1988) "Production of Hybrid Seed", *Corn and Corn Improvement*, Ch. 9, pp. 565–607.
Meghji et al. 1984. Crop Science. 24: 545–549.
Green et al. 1975. Crop Science. 15: 417–421.
Hallauer et al. 1988. In Corn and Corn Improvement. Sprague et al. eds. Ch. 8: 463–564.

*Primary Examiner*—Erich E. Veitenheimer

[57] ABSTRACT

According to the invention, there is provided a hybrid corn plant, designated as 3893, produced by crossing two Pioneer Hi-Bred International, Inc. proprietary inbred corn lines. This invention thus relates to the hybrid seed 3893, the hybrid plant produced from the seed, and variants, mutants and trivial modifications of hybrid 3893. This hybrid corn plant is characterized by excellent yield for maturity and excellent stalks. 3893 has very good stand establishment and is higher in protein than other hybrids in its maturity. 3893 has above average performance across all yield environments and responds very well to high yield environments.

5 Claims, 1 Drawing Sheet

FIG. 1

HYBRID CORN PLANT (3893)

This application is a continuation of prior application Ser. No. 08/187,966, filed Jan. 28, 1994, now abandoned.

FIELD OF THE INVENTION

This invention is in the field of corn breeding, specifically relating to an hybrid corn plant designated 3893.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Hybrid corn seed can be produced by manual detasseling. Alternate strips of two inbred varieties of corn are planted in a field, and the pollen-bearing tassels are removed from one of the inbreds (female). Providing that there is sufficient isolation from sources of foreign corn pollen, the ears of the detasseled inbred will be fertilized only from pollen from the other inbred (male), and the resulting seed is therefore hybrid and will form hybrid plants.

The laborious detasseling process can be avoided by using male-sterile inbreds. Plants of these inbreds are fertilized with pollen from another inbred that is not male-sterile. Pollen from the second inbred can contribute genes that make the hybrid plants male-fertile. Usually seed from detasseled normal corn and male sterile produced seed of the same hybrid is blended to insure that adequate pollen loads are available for fertilization when the hybrid plants are grown.

The objective of commercial maize hybrid line development programs is to develop new inbred lines to produce hybrids that combine to produce high grain yields and superior agronomic performance. The primary trait breeders seek is yield. However, other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes.

Pedigree Breeding

The pedigree method of breeding is the mostly widely used methodology for new hybrid line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

EXAMPLE 1

Hypothetical Example of Pedigree Breeding Program

Consider a cross between two inbred lines that differ for alleles at five loci.
The parental genotypes are:

| Parent 1 | A | b | C | d | e | F/A | b | C | d | e | F |
|---|---|---|---|---|---|---|---|---|---|---|---|
| Parent 2 | a | b | c | D | E | f/a | B | c | D | E | f | the $F_1$ from a cross between these two parents is:

| $F_1$ | A | b | C | d | e | F/a | B | c | D | E | f |
|---|---|---|---|---|---|---|---|---|---|---|---|

Selfing $F_1$ will produce an $F_2$ generation including the following genotypes:

| A | B | c | D | | E | f/a | b | C | d | e | F |
|---|---|---|---|---|---|---|---|---|---|---|---|
| A | B | c | D | | e | f/a | b | C | d | E | F |
| A | B | c | D | | e | f/a | b | C | d | e | F |

.
.
.

The number of genotypes in the $F_2$ is $3^6$ for six segregating loci (729) and will produce $(2^6)-2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, *TAG* 80:833–840 (1990)) that each of these lines are different and can be uniquely identified on the basis of genetically-controlled molecular markers.

It has been shown (Hallauer, Arnel R. and Miranda, J. B. Fo. *Quantitative Genetics in Maize Breeding,* Iowa State University Press, Ames Iowa, 1981) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D. N., *Maydica* 37:69–79, (1992); Russell, W. A., *Maydica* XXIX:375–390 (1983)) have shown that over the last 50 years the rate of genetic progress in commercial hybrids has been between 1 and 2% per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience suggests that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ and the number of unique inbred lines from this cross is $\{(2^n)-2\}$. Only a very limited number of these combinations are useful. Only about 1 in 10,000 of the progeny from $F_2$'s are commercially useful.

By way of example, if it is assumed that the number of segregating loci in $F_2$ is somewhere between 20 and 50, and that each parent is fixed for half the favorable alleles, it is then possible to calculate approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)+m favorable alleles will exist.

To put this in perspective the number of plants grown on 60 million acres (approximate US corn acreage) at 25000 plants/acre is $1.5 \times 10^{12}$.

EXAMPLE 2

Probability of Finding an Inbred with m of n Favorable Alleles

Assume each parent has n/2 of the favorable alleles and only ½ of the combinations of loci are economically useful.

| no. of segregating loci (n) | no. favorable alleles in Parents (n/2) | no. additional favorable alleles in new inbred | Probability that genotype occurs* |
| --- | --- | --- | --- |
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

At Pioneer Hi-Bred International, a typical corn research station has a staff of four, and 20 acres of breeding nursery. Those researchers plant those 20 acres with 25,000 nursery rows, 15,000 yield test plots in 10–15 yield test sites, and one or two disease-screening nurseries. Employing a temporary crew of 20 to 30 pollinators, the station makes about 65,000 hand pollinations per growing season. Thus, one of the largest plant breeding programs in the world does not have a sufficiently large breeding population to be able to rely upon "playing the numbers" to obtain successful research results. Nevertheless, Pioneer's breeders at each station produce from three to ten new inbreds which are proposed for commercial use each year. Over the 32 Pioneer research stations in North America, this amounts to from about 100 to 300 new inbreds proposed for use, and less than 50 and more commonly less than 30 of these inbreds that actually satisfy the performance criteria for commercial use.

This is a result of plant breeders using their skills, experience, and intuitive ability to select inbreds having the necessary qualities so that improved hybrids may be produced.

SUMMARY OF THE INVENTION

According to the invention, there is provided a hybrid corn plant, designated as 3893, seed of which has been deposited with the American Type Culture Collection; 12301 Parklawn Drive, Rockville, Md., 20852, on May 29, 1996, and having ATCC accession no. 97588. This invention thus relates to the hybrid seed 3893, the hybrid plant produced from the seed, and variants, mutants and trivial modifications of hybrid 3893. 3893 is characterized by its exceptional yield and is widely adapted across a broad range of yield environments. 3893 is an attractive hybrid with good root lodging resistance. The hybrid is an excellent silage hybrid with good digestibility. 3893 performs well across a wide range of environments.

DEFINITIONS

In the description and examples that follow, a number of terms are used herein. In order to provide a clear and consistent understanding of the specification and claims, including the scope to be given such terms, the following definitions are provided. ABS is in absolute terms and % MN is percent of the mean for the experiments in which the inbred or hybrid was grown.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest in bushels per acre adjusted to 15.5% moisture.

DRP EAR=DROPPED EARS. A measure of the number of dropped ears per plot and represents the percentage of plants that did not drop ears prior to harvest.

EAR HT=EAR HEIGHT. The ear height is a measure from the ground to the highest placed developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a $$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic factors, be produced in a cytoplasmic male-sterile form which is otherwise phenotypically identical to the male-fertile form.

PRM=PREDICTED RM. This trait, predicted relative maturity (RM), is based on the harvest moisture of the grain. The relative maturity rating is based on a known set of checks and utilizes standard linear regression analyses and is referred to as the Comparative Relative Maturity Rating System which is similar to the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV=Maize Dwarf Mosaic Virus & MCDV=Maize Chlorotic Dwarf Virus): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Pioneer Brand Hybrid 3893 is an exceptionally yielding, broadly adapted hybrid that has an attractive field appearance. The hybrid has good root lodging resistance which is needed in this maturity and has very good early growth. The hybrid has excellent silage yield and digestibility. 3893 has above average brittle stalk resistance and performs well across a wide range of environments, including Europe.

Pioneer Brand Hybrid 3893 is a single cross, yellow endosperm, dent corn hybrid with exceptional yield for its maturity. 3893 responds favorably to increasingly favorable environments and will be an excellent silage hybrid.

This hybrid has the following characteristics based on the descriptive data collected primarily at Johnston, Iowa.

VARIETY DESCRIPTION INFORMATION

HYBRID=PIONEER BRAND 3893

Type: Dent
Region Best Adapted: North
A. Maturity
  Minnesota Relative Maturity Rating (harvest moisture): 89
  GDU's to Physiological Maturity (black layer): 2040
  GDU's to 50% Silk: 1070

$$GDU\text{'s} = \frac{[\text{Max. Temp. }(\leq 86°\text{ F.}) + \text{Min. Temp}(\geq 50°\text{ F.})]^*}{2} - 50$$

*If maximum is greater than 86 degrees fahrenheit, then 86 is used and if minimum is less than 50, then 50 is used. Heat units accumulated daily and can not be less than 0.

B. Plant Characteristics
  Plant height (to tassel tip): 241 cm
  Length of top ear internode: 17 cm
  Number of ears per stalk: Single
  Ear height (to base of top ear): 68 cm
  Number of tillers: None
  Cytoplasm type: Normal
C. Leaf
  Color: (B14) Dark Green
  Angle from Stalk: 30–60 degrees
  Marginal Waves: (WF9) Few
  Number of Leaves (mature plants): 17
  Sheath Pubescence: (W22) Light
  Longitudinal Creases: (OH56A) Few
  Length (Ear node leaf): 85 cm
  Width (widest point, ear node leaf): 9 cm
D. Tassel
  Number lateral branches: 5
  Branch Angle from central spike: >45 degrees
  Pollen Shed: (KY21) Heavy
  Peduncle Length (top leaf to basal branches): 23 cm
  Anther Color: Purple
  Glume Color: Green
E. Ear (Husked Ear Data Except When Stated Otherwise)
  Length: 17 cm
  Weight: 162 gm
  Mid-point Diameter: 45 mm
  Silk Color: Yellow
  Husk Extension (Harvest stage): Medium (Barely Covering Ear)
  Husk Leaf: Long (>15 cm)
  Taper of Ear: Average
  Position of Shank (dry husks): Upright
  Kernel Rows: Slightly Curved Distinct Number=14
  Husk Color (fresh): Light Green
  Husk Color (dry): Buff
  Shank Length: 17 cm
  Shank (No. of internodes): 8
F. Kernel (Dried)
  Size (from ear mid-point)
    Length: 12 mm
    Width: 9 mm
    Thick: 4 mm
  Shape Grade (% rounds): N/A
  Pericarp Color: Colorless
  Aleurone Color: Homozygous Yellow
  Endosperm Color: Yellow
  Endosperm Type: Normal Starch
  Gm Wt/100 Seeds (unsized): 32 gm
G. Cob
  Diameter at mid-point: 25 mm
  Strength: Strong
  Color: Red
H. Diseases
  N. Leaf Blight (*E. turcicum*): Intermediate
  Goss's Wilt (*C. nebraskense*): Highly Resistant
  Head Smut (*S. reiliana*): Resistant
  Gibberella Ear Rot (*G. zeae*): Intermediate
I. Insects
  The above descriptions are based on a scale of 1–9, 1 being highly susceptible, 9 being highly resistant.
  S (Susceptible): would generally represent a score of 1–3.
  I (Intermediate): Would generally represent a score of 4–5.
  R (Resistant): Would generally represent a score of 6–7.
  H (Highly Resistant): Would generally represent a score of 8–9. Highly resistant does not imply the inbred is immune.
J. Variety Most Closely Resembling

| Character | Hybrid |
| --- | --- |
| Maturity | Pioneer Brand 3845 |
| Usage | Pioneer Brand 3845 |

Items B, C, D, E, F, and G are based on a maximum of two reps of data primarily from Johnston, Iowa in 1993.

EXAMPLE 1

Research Comparisons for Pioneer Hybrid 3893

Comparisons of the characteristics for Pioneer Brand Hybrid 3893 were made against Pioneer Brand Hybrids 3876, 3861, 3845 and 3795. Table 1A shows Pioneer Brand Hybrid 3893 has higher yield and lower grain harvest moisture and test weight than Pioneer Hybrid 3876. 3893 is a shorter hybrid with higher ear placement and flowers (GDU Shed and GDU Silk) earlier than 3876. 3893 has significantly better seedling vigor and early stand establishment than 3876.

Table 1B compares Pioneer Brand Hybrid 3893 to Pioneer Brand Hybrid 3861. 3893 has significantly higher yield and test weight but lower grain harvest moisture than 3861. 3893 is a shorter hybrid with lower ear placement and flowers (GDU Shed and GDU Silk) earlier than 3861. Compared to 3861, 3893 has better seedling vigor and early stand count. Though more susceptible to stalk lodging, 3893 has significantly better root lodging resistance than 3861.

The results in Table 1C, comparing Pioneer Brand Hybrid 3893 to Pioneer Brand Hybrid 3845, shows 3893 has higher yield and test weight but lower grain harvest moisture than 3845. 3893 is shorter with lower ear placement and flowers (GDU Shed and GDU Silk) significantly earlier than 3845. 3893 has a higher early stand count than 3845.

Table 1D compares Pioneer Brand Hybrid 3893 to Pioneer Brand Hybrid 3795. The data shows 3893 has significantly higher yield and lower grain harvest moisture and test weight compared to 3795. 3893 is shorter with lower ear placement and flowers (GDU Shed and GDU Silk) earlier than 3795. 3893 has significantly better seedling vigor and significantly higher early stand count compared to 3795. 3893 has significantly better brittle stalk resistance than 3795.

TABLE 1A

Figure 1:
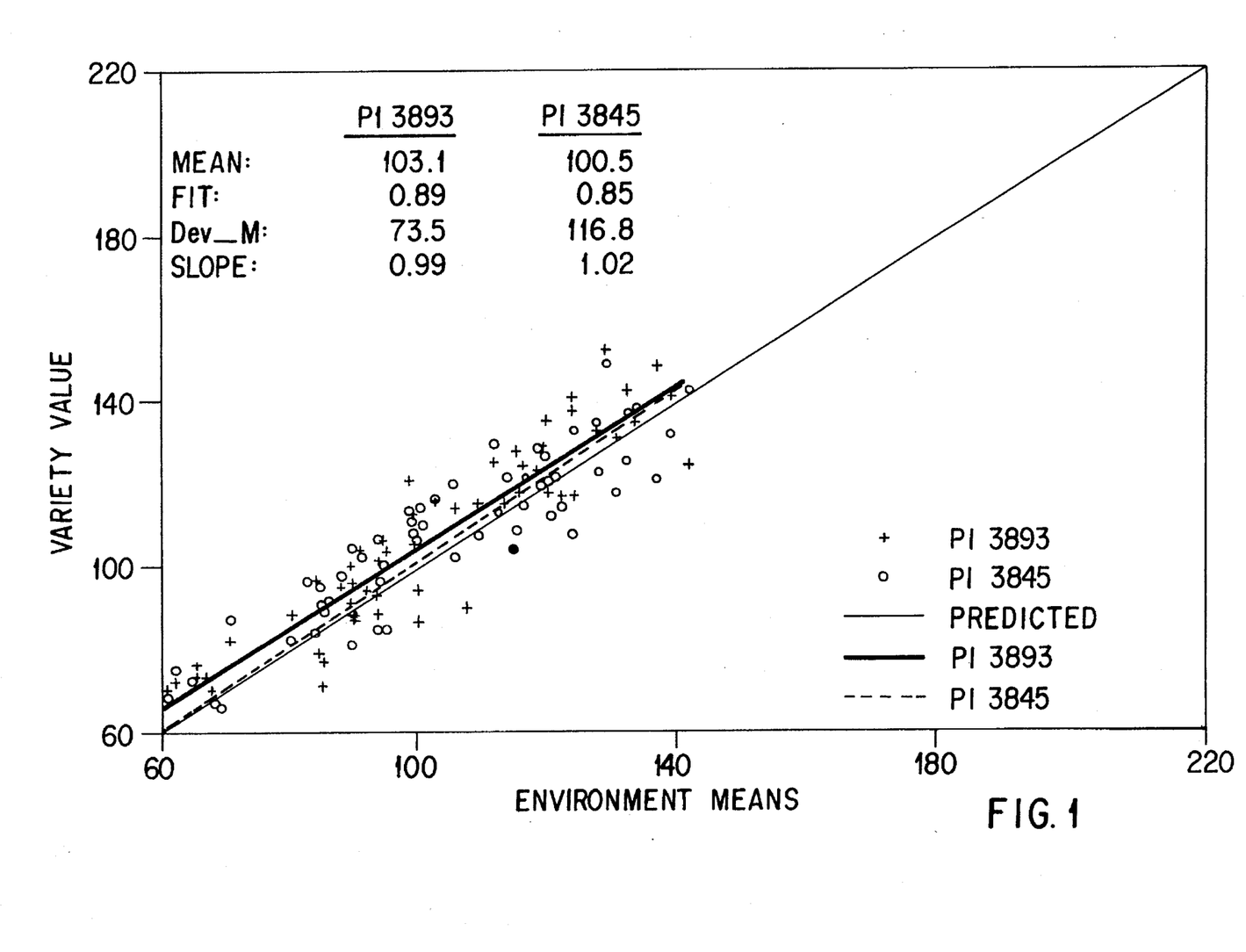
FIG. 1 compares the yield response of Pioneer Brand Hybrid 3893, to increasingly favorable conditions, to Pioneer Brand 3845. Both hybrids have above average yield, with 3893 having a higher yield over all environments than 3845.

VARIETY #1 - 3893
VARIETY #2 - 3876

|  | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|
| TOTAL SUM | 1 | 107.8 | 109 | 27.3 | 96.9 | 41.5 | 6.2 | 74.3 | 100.0 |
|  | 2 | 98.9 | 100 | 28.0 | 99.7 | 39.2 | 5.4 | 72.6 | 99.8 |
|  | LOCS | 81 | 81 | 80 | 51 | 51 | 66 | 46 | 37 |
|  | REPS | 122 | 122 | 120 | 74 | 74 | 90 | 70 | 49 |
|  | DIFF | 8.8 | 8 | 0.7 | 2.8 | 2.3 | 0.8 | 1.7 | 0.2 |
|  | PROB | .000# | .000# | .031+ | .000# | .003# | .000# | .027+ | .095* |

|  | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1090 | 1060 | 49.7 | 5.4 | 5.5 | 88.3 | 97.6 | 98.8 |
|  | 2 | 1100 | 1074 | 50.4 | 5.5 | 5.9 | 91.2 | 95.9 | 96.8 |
|  | LOCS | 21 | 7 | 61 | 36 | 9 | 71 | 11 | 7 |
|  | REPS | 38 | 13 | 88 | 52 | 16 | 103 | 14 | 9 |
|  | DIFF | 10 | 14 | 0.7 | 0.1 | 0.5 | 2.9 | 1.7 | 1.9 |
|  | PROB | .007# | .315 | .000# | .466 | .272 | .014+ | .151 | .321 |

* = 10% SIG
+ = 5% SIG
# = 1% SIG

TABLE 1B

VARIETY #1 - 3893
VARIETY #2 - 3861

|  | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|
| TOTAL SUM | 1 | 110.5 | 106 | 26.3 | 93.5 | 39.8 | 5.9 | 72.2 | 99.9 |
|  | 2 | 106.5 | 102 | 28.0 | 103.4 | 40.5 | 5.4 | 70.9 | 99.9 |
|  | LOCS | 231 | 231 | 229 | 143 | 141 | 191 | 161 | 145 |
|  | REPS | 331 | 331 | 329 | 220 | 218 | 276 | 259 | 217 |
|  | DIFF | 4.1 | 4 | 1.7 | 9.9 | 0.7 | 0.5 | 1.3 | 0.0 |
|  | PROB | .000# | .000# | .000# | .000# | .038+ | .000# | .000# | .922 |

|  | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1087 | 1051 | 50.6 | 5.3 | 4.0 | 86.4 | 95.4 | 95.1 |
|  | 2 | 1119 | 1096 | 49.6 | 5.5 | 4.9 | 93.7 | 80.9 | 97.2 |
|  | LOCS | 64 | 14 | 169 | 91 | 36 | 194 | 25 | 18 |

TABLE 1B-continued

VARIETY #1 - 3893
VARIETY #2 - 3861

|  |  |  |  |  |  |  |  |  |
|---|---|---|---|---|---|---|---|---|
| REPS | 100 | 22 | 248 | 152 | 61 | 292 | 30 | 20 |
| DIFF | 32 | 45 | 1.0 | 0.2 | 0.9 | 7.3 | 14.6 | 2.1 |
| PROB | .000# | .000# | .000# | .046+ | .010+ | .000# | .003# | .105 |

* = 10% SIG
+ = 5% SIG
# = 1% SIG

TABLE 1C

VARIETY #1 - 3893
VARIETY #2 - 3845

|  | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|
| TOTAL SUM | 1 | 112.2 | 107 | 26.8 | 94.9 | 40.8 | 6.0 | 72.1 | 99.9 |
|  | 2 | 107.6 | 102 | 28.0 | 104.9 | 42.1 | 6.5 | 71.3 | 99.9 |
|  | LOCS | 180 | 180 | 177 | 104 | 102 | 149 | 121 | 114 |
|  | REPS | 269 | 269 | 264 | 161 | 159 | 218 | 193 | 172 |
|  | DIFF | 4.5 | 5 | 1.2 | 10.0 | 1.3 | 0.5 | 0.7 | 0.0 |
|  | PROB | .000# | .000# | .000# | .000# | .001# | .000# | .060* | .970 |

|  | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1082 | 1051 | 50.7 | 5.3 | 4.8 | 88.9 | 96.2 | 96.8 |
|  | 2 | 1132 | 1109 | 49.8 | 5.6 | 6.6 | 94.0 | 93.4 | 98.6 |
|  | LOCS | 49 | 13 | 135 | 66 | 21 | 157 | 17 | 13 |
|  | REPS | 78 | 21 | 198 | 109 | 37 | 239 | 21 | 16 |
|  | DIFF | 50 | 58 | 0.9 | 0.2 | 1.8 | 5.2 | 2.8 | 1.8 |
|  | PROB | .000# | .000# | .000# | .050* | .000# | .000# | .198 | .193 |

* = 10% SIG
+ = 5% SIG
# = 1% SIG

TABLE 1D

VARIETY #1 - 3893
VARIETY #2 - 3795

|  | VAR # | BU ACR ABS | BU ACR % MN | MST ABS | PLT HT ABS | EAR HT ABS | SDG VGR ABS | EST CNT ABS | DRP EAR ABS |
|---|---|---|---|---|---|---|---|---|---|
| TOTAL SUM | 1 | 116.0 | 109 | 26.6 | 97.2 | 41.0 | 6.2 | 71.7 | 99.9 |
|  | 2 | 105.7 | 98 | 29.0 | 100.1 | 42.1 | 5.5 | 69.6 | 99.7 |
|  | LOCS | 68 | 68 | 68 | 41 | 41 | 46 | 42 | 29 |
|  | REPS | 100 | 100 | 100 | 61 | 61 | 64 | 65 | 43 |
|  | DIFF | 10.3 | 11 | 2.4 | 2.9 | 1.0 | 0.7 | 2.0 | 0.3 |
|  | PROB | .000# | .000# | .000# | .000# | .088* | .003# | .004# | .155 |

|  | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1105 | 1097 | 50.4 | 5.4 | 5.3 | 86.0 | 95.1 | 97.5 |
|  | 2 | 1116 | 1108 | 51.1 | 5.6 | 6.3 | 91.8 | 94.2 | 72.1 |
|  | LOCS | 21 | 6 | 51 | 36 | 11 | 62 | 9 | 5 |
|  | REPS | 36 | 11 | 74 | 55 | 17 | 93 | 11 | 6 |
|  | DIFF | 11 | 11 | 0.7 | 0.2 | 1.0 | 5.8 | 0.9 | 25.4 |
|  | PROB | .054* | .146 | .000# | .177 | .048+ | .000# | .204 | .070* |

* = 10% SIG
+ = 5% SIG
# = 1% SIG

EXAMPLE 2

Strip Test Data for Hybrid 3893

Comparison data was collected from strip tests that were grown by farmers. Each hybrid was grown in strips of 4, 6, 8, 12, etc. rows in fields depending on the size of the planter used. The data was collected from strip tests that had the hybrids in the same area and weighed. The moisture percentage was determined and bushels per acre was adjusted to 15.5 percent moisture. The number of comparisons represent the number of locations or replications for the two hybrids that were grown in the same field in close proximity and compared.

Comparison strip testing was done between Pioneer Brand Hybrid 3893 and Pioneer Brand Hybrids 3876, 3861, 3845 and 3795. The comparisons came from all the hybrids' adapted growing areas in the United States.

These results are presented in Table 2. 3893 has a yield and moisture advantage over the hybrids compared. 3893 has a significant income per acre advantage over the hybrids compared, ranging from $5.50 to $17.57. The yield and income per acre advantage 3893 provides in its area of adapation, plus its other agronomic characteristics, will make it an important addition for most of the areas where these hybrids are grown.

on a 1–9 basis. In these cases 9 would be outstanding, while 1 would be poor for the given characteristics. These values are based on performance of a given hybrid relative to other Pioneer commercial, precommercial and competitive hybrids that are grown in research and strip test trials. The traits characterized in Table 3 were defined previously and the ratings utilized not only research data but experience trained corn researchers had in the field as well as sales experience with the hybrids in strip tests and the field. These scores reflect the hybrid's relative performance to other hybrids for the characteristics listed. Table 3 shows 3893 yielded well for its maturity, both in high and low plant densities. 3893 has comparable drydown, and above average root lodging resistance and staygreen compared to the other hybrids. Compared to the other hybrids, 3893 has good grain appearance and excellent seedling vigor. 3893 is a shorter hybrid compared to the other hybrids. 3893 has overall excellent yield and agronomic characteristics which should make it an important hybrid in its area of adaptation.

TABLE 2

PIONEER HYBRID 3893 VS PIONEER HYBRIDS 3876, 3861, 3845 AND 3795 FROM 1993 STRIP TESTS

| Brand | Product | Yield | Moist | Income /Acre | Pop K/Acre | Stand (%) | Roots (%) | Test Wt |
|---|---|---|---|---|---|---|---|---|
| PIONEER | 3893 | 125.9 | 26.0 | 257.03 | 27.0 | 93 | 84 | 51.2 |
| PIONEER | 3876 | 118.4 | 27.1 | 239.46 | 27.0 | 95 | 90 | 51.5 |
| Advantage | | 7.5 | 1.1 | 17.57 | 0.0 | −2 | −6 | −0.3 |
| Number of Comparisons | | 92 | 92 | 92 | 78 | 71 | 47 | 74 |
| Percent Wins | | 79 | 73 | 80 | 42 | 33 | 19 | 22 |
| Probability of Difference | | 99 | 99 | 99 | 1 | 94 | 53 | 95 |
| PIONEER | 3893 | 107.0 | 24.0 | 223.09 | 26.6 | 89 | 88 | 51.0 |
| PIONEER | 3861 | 104.6 | 25.3 | 215.74 | 26.6 | 93 | 82 | 49.3 |
| Advantage | | 2.4 | 1.3 | 7.35 | 0.0 | −4 | 6 | 1.7 |
| Number of Comparisons | | 161 | 161 | 161 | 114 | 104 | 75 | 143 |
| Percent Wins | | 60 | 65 | 62 | 42 | 29 | 37 | 87 |
| Probability of Difference | | 99 | 99 | 99 | 6 | 99 | 99 | 99 |
| PIONEER | 3893 | 102.3 | 23.9 | 213.96 | 26.8 | 87 | 87 | 50.8 |
| PIONEER | 3845 | 99.9 | 24.8 | 208.46 | 27.1 | 93 | 87 | 49.6 |
| Advantage | | 2.4 | 0.9 | 5.50 | −0.3 | −6 | 0 | 1.2 |
| Number of Comparisons | | 83 | 83 | 83 | 52 | 50 | 38 | 77 |
| Percent Wins | | 54 | 55 | 57 | 38 | 20 | 7 | 68 |
| Probability of Difference | | 90 | 99 | 92 | 54 | 99 | 40 | 99 |
| PIONEER | 3893 | 127.5 | 26.2 | 259.59 | 27.3 | 91 | 99 | 51.6 |
| PIONEER | 3795 | 121.3 | 28.3 | 242.50 | 27.4 | 94 | 98 | 51.8 |
| Advantage | | 6.2 | 2.1 | 17.39 | −0.1 | −3 | 1 | −0.2 |
| Number of Comparisons | | 65 | 65 | 65 | 55 | 52 | 36 | 54 |
| Percent Wins | | 83 | 90 | 84 | 40 | 26 | 16 | 16 |
| Probability of Difference | | 99 | 99 | 99 | 28 | 98 | 75 | 86 |
| PIONEER | 3893 | 113.7 | 24.8 | 234.90 | 26.9 | 90 | 89 | 51.1 |
| WEIGHTED AVG | | 109.5 | 26.1 | 223.96 | 26.9 | 93 | 88 | 50.2 |
| Advantage | | 4.2 | 1.3 | 10.94 | 0.0 | −3 | 1 | 0.9 |
| Number of Comparisons | | 401 | 401 | 401 | 299 | 277 | 196 | 348 |
| Percent Wins | | 67 | 69 | 69 | 41 | 28 | 23 | 58 |
| Probability of Difference | | 99 | 99 | 99 | 35 | 99 | 39 | 99 |

EXAMPLE 3

Comparison of Key Characteristics for Hybrid 3893

Characteristics of Pioneer Brand Hybrid 3893 are compared to Pioneer Brand Hybrids 3876, 3861, 3845 and 3795 in Table 3. The ratings given for most of the traits are given

TABLE 3

HYBRID PATENT COMPARISONS-CHARACTERISTICS
Pioneer Hybrid 3893 vs Pioneer Hybrids 3876, 3861, 3845 and 3795

| HYBRID | SILK CRM | GDU SILK | BL CRM | GDU BL | CRM | YLD | H/POP | L/POP | D/D | S/L |
|---|---|---|---|---|---|---|---|---|---|---|
| 3893 | 89 | 1140 | 86 | 2200 | 89 | 9 | 9 | 8 | 6 | 4 |
| 3876 | 90 | 1150 | 89 | 2270 | 90 | 9 | 9 | 8 | 5 | 5 |
| 3861 | 94 | 1200 | 94 | 2420 | 93 | 9 | 9 | 8 | 7 | 7 |
| 3845 | 94 | 1200 | 96 | 2440 | 91 | 8 | 8 | 7 | 6 | 6 |
| 3795 | 91 | 1160 | 90 | 2300 | 92 | 8 | 8 | 7 | 6 | 7 |

| HYBRID | R/L | STGR | D/T | T/WT | G/A | E/G | P/HT | E/HT | D/E | B/STK |
|---|---|---|---|---|---|---|---|---|---|---|
| 3893 | 7 | 8 | — | 5 | 6 | 8 | 5 | 6 | 5 | 5 |
| 3876 | 6 | 3 | — | 6 | 4 | 5 | 6 | 5 | 5 | 3 |
| 3861 | 4 | 6 | 7 | 3 | 7 | 5 | 8 | 7 | 6 | 8 |
| 3845 | 6 | 7 | 5 | 4 | 5 | 8 | 8 | 6 | 4 | 7 |
| 3795 | 4 | 6 | 6 | 7 | 5 | 7 | 6 | 7 | 5 | 2 |

INDUSTRIAL APPLICABILITY

This invention includes hybrid corn seed of 3893 and the hybrid corn plant produced therefrom. The foregoing was set forth by way of example and is not intended to limit the scope of the invention.

As used herein, the term plant includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Duncan, Williams, Zehr, and Widholm, *Planta*, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in *Plant Cell Reports* (1988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64–65 (1986), refers to somatic embryogenesis from glume callus cultures and B. V. Conger, et al., *Plant Cell Reports*, 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367–372) and in Duncan, et al., "The Production of Callus Capable of Plant Regeneration from Immature Embryos of Numerous Zea Mays Genotypes," 165 *Planta* 322–332 (1985). Thus, another aspect of this invention is to provide cells which upon growth and differentiation produce corn plants having the genotype of 3893.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of the hybrid corn plant and various parts of the hybrid corn plant can be utilized for human food, livestock feed, and as a raw material in industry.

Although the foregoing invention has been described in some detail by way of illustration and example for purposes of clarity and understanding, it will be obvious that certain changes and modifications may be practiced within the scope of the invention, as limited only by the scope of the appended claims.

DEPOSITS

A deposit of the hybrid seed of this invention is maintained by Pioneer Hi-Bred International, Inc., 700 Capital Square, 400 Locust Street, Des Moines, Iowa 50390. Access to this deposit will be available during the pendency of this application to the Commissioner of Patents and Trademarks and to persons determined by the Commissioner to be entitled thereto upon request. Upon allowance of any claims in this application, all restrictions on availability to the public of such material will be removed by affording access to a deposit with the American Type Culture Collection, Rockville, Md. of at least 2500 seeds of the hybrid, taken from the deposit maintained by Pioneer Hi-Bred International, Inc. The deposit will conform with the requirements of 37 C.F.R. §§1.801–1.809, will be maintained in that depository, which is a public depository, for a period of 30 years, or 5 years after the last request, or the effective life of the patent, whichever is longer, and will be replaced if it becomes nonviable during that period.

What is claimed is:

1. A hybrid corn plant designated 3893, seed of said hybrid having ATCC accession number 97588.

2. A corn plant having all of the physiological and morphological characteristics of a hybrid corn plant designated 3893, seed of said hybrid corn plant designated 3893 having ATCC accession number 97588.

3. A tissue culture of regenerable cells of a corn plant designated hybrid 3893 wherein the tissue culture regenerates plants having all of the physiological and morphological characteristics of hybrid 3893, seed of said hybrid 3893 having ATCC accession number 97588.

4. A tissue culture according to claim 3, the tissue culture selected from the group consisting of leaves, pollen, embryos, roots, root tips, anthers, silks, flowers, kernels, ears, cobs, husks, stalks, and cells and protoplasts thereof.

5. A corn plant regenerated from the tissue culture of claim 3 and having all of the physiological and morphological characteristics of hybrid 3893, seed of said hybrid 3893 having ATCC accession number 97588.

* * * * *